United States Patent
Bouton et al.

(10) Patent No.: US 8,295,920 B2
(45) Date of Patent: Oct. 23, 2012

(54) SYSTEM FOR DETECTING FLUID CHANGES AND SENSORING DEVICES THEREFOR

(75) Inventors: Chad E. Bouton, Delaware, OH (US); Felicia R. Ruggeri, Columbus, OH (US); R. Reade Harpham, Columbus, OH (US); Jeffrey R. Held, Columbus, OH (US)

(73) Assignee: Medrad, Inc., Indianola, PA (US)

( * ) Notice: Subject to any disclaimer, the term of this patent is extended or adjusted under 35 U.S.C. 154(b) by 1470 days.

(21) Appl. No.: 10/576,333

(22) PCT Filed: Oct. 25, 2004

(86) PCT No.: PCT/US2004/035135
§ 371 (c)(1),
(2), (4) Date: Apr. 18, 2006

(87) PCT Pub. No.: WO2005/043100
PCT Pub. Date: May 12, 2005

(65) Prior Publication Data
US 2007/0123770 A1 May 31, 2007

Related U.S. Application Data

(60) Provisional application No. 60/514,355, filed on Oct. 24, 2003.

(51) Int. Cl.
*A61B 5/05* (2006.01)
(52) U.S. Cl. ........ 600/547; 600/307; 600/382; 600/384; 600/393; 600/398; 600/407; 600/473; 600/475; 600/476; 600/477
(58) Field of Classification Search .................. 600/307, 600/398, 407, 473, 475, 476, 477
See application file for complete search history.

(56) References Cited

U.S. PATENT DOCUMENTS
4,240,445 A 12/1980 Iskander et al.
(Continued)

FOREIGN PATENT DOCUMENTS
WO 03009753 2/2003
(Continued)

OTHER PUBLICATIONS

Birnbaum et al.,"Extravasation Detection Accessory: Clinical Evaluation in 500 Patients," Radiology (1999;212:431-438.).

(Continued)

*Primary Examiner* — Tse Chen
*Assistant Examiner* — Jason Ip
(74) *Attorney, Agent, or Firm* — Jim Denesvich

(57) ABSTRACT

A sensor device for detecting a change fluid level within body tissue comprising a housing with bridge segments connecting at intersections arranged to circumscribe an opening. Further, antenna elements are partially seated within the housing at intersections of bridge segments, comprise a generally planar antenna mounted to a substrate material at a base of the planar antenna, and an electrical shield surrounding the substrate. Also, an outer surface of the planar antenna faces away from the substrate. The antenna elements comprise at least first and second antenna element pairs having transmitting and receiving antenna elements and a bridging segment. A high sensitivity zone is formed between the transmitting antenna and receiving antenna. The antenna element pairs are spaced to create an area of reduced sensitivity between the high sensitivity zones, and the space is set so that the sensor is insensitive to fluid changes of a predetermined volume.

19 Claims, 8 Drawing Sheets

U.S. PATENT DOCUMENTS

| | | | |
|---|---|---|---|
| 4,488,559 A | 12/1984 | Iskander | |
| 4,647,281 A | 3/1987 | Carr | |
| 4,690,149 A | 9/1987 | Ko | |
| 4,877,034 A | 10/1989 | Atkins et al. | |
| 5,184,620 A * | 2/1993 | Cudahy et al. | 600/382 |
| 5,334,141 A | 8/1994 | Carr et al. | |
| 5,947,910 A | 9/1999 | Zimmet | |
| 5,954,668 A | 9/1999 | Uber, III et al. | |
| 5,964,703 A | 10/1999 | Goodman et al. | |
| 5,995,863 A | 11/1999 | Farace et al. | |
| 6,026,173 A | 2/2000 | Svenson et al. | |
| 6,047,215 A | 4/2000 | McClure et al. | |
| 6,061,589 A | 5/2000 | Bridges et al. | |
| 6,233,479 B1 | 5/2001 | Haddad et al. | |
| 6,263,226 B1 | 7/2001 | Axelgaard et al. | |
| 6,300,906 B1 | 10/2001 | Rawnick et al. | |
| 6,332,087 B1 | 12/2001 | Svenson et al. | |
| 6,408,204 B1 * | 6/2002 | Hirschman | 600/547 |
| 6,415,170 B1 | 7/2002 | Loutis et al. | |
| 6,487,428 B1 * | 11/2002 | Culver et al. | 600/310 |
| 7,122,012 B2 | 10/2006 | Bouton et al. | |
| 2003/0004433 A1 | 1/2003 | Hirschman | |
| 2003/0036674 A1 | 2/2003 | Bouton | |
| 2003/0036713 A1 | 2/2003 | Bouton et al. | |

FOREIGN PATENT DOCUMENTS

| | | |
|---|---|---|
| WO | 03/063680 A2 | 8/2003 |

OTHER PUBLICATIONS

Kent, M., "Hand Held Instrument for Fat/Water Determination in Whole Fish" (1993) at http://www.distell.com/index.php?exe=products:fish%20fat%20meter:research%20paper.

Supplementary European Search Report, May 26, 2010.

* cited by examiner

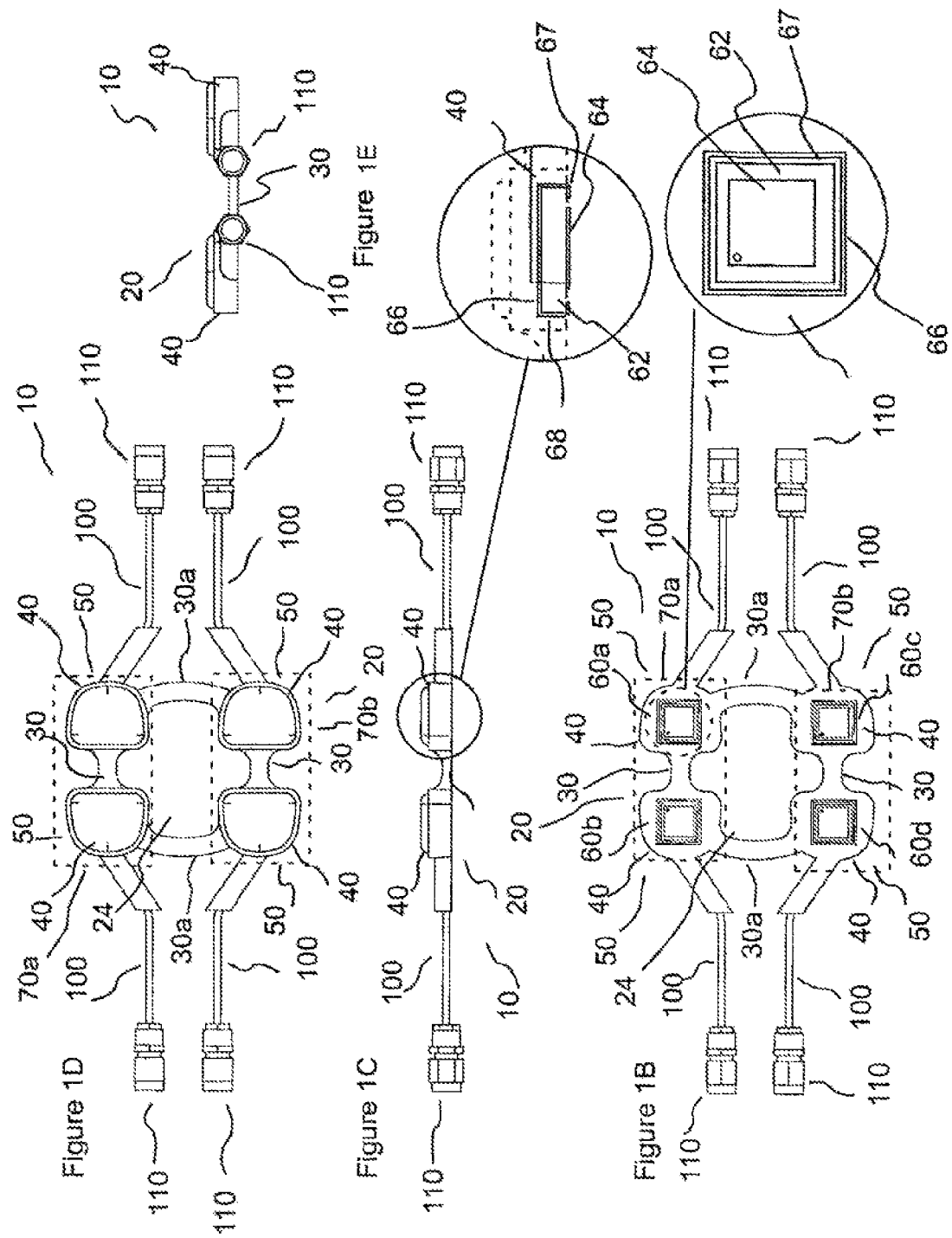

SYSTEM FOR DETECTING FLUID CHANGES AND SENSORING DEVICES THEREFOR

CROSS-REFERENCE TO RELATED APPLICATION

This application claims benefit of U.S. Provisional Patent Application Ser. No. 60/514,355, filed Oct. 24, 2003, the disclosure of which is incorporated herein by reference.

BACKGROUND OF THE INVENTION

The present invention relates generally to the detection of fluid and/or other material in tissue, and especially, to systems, methods and/or devices for detecting changes in the level of fluid in tissue. In certain embodiments, the systems, methods and/or devices of the present invention detect if fluid level has increased or, has otherwise become abnormal.

The following information is provided to assist the reader to understand the invention disclosed below and the environment in which it will typically be used. The terms used herein are not intended to be limited to any particular narrow interpretation unless clearly stated otherwise in this document. References set forth herein may facilitate understanding of the present invention or the background of the present invention. Inclusion of a reference herein, however, is not intended to and does not constitute an admission that the reference is available as prior art with respect to the present invention Changed, elevated or abnormal fluid levels in living tissue can result from a number of physiological conditions. For example, edema is an abnormal accumulation of watery fluid in the intercellular spaces of connective tissue. Edematous tissues are swollen and, when punctured, secrete a thin incoagulable fluid. Edema is most frequently a symptom of disease rather than a disease in itself, and it may have a number of causes, most of which can be traced back to gross variations in the physiological mechanisms that normally maintain a constant water balance in the cells, tissues, and blood. Among the causes may be diseases of the kidneys, heart, veins, or lymphatic system; malnutrition; or allergic reactions.

Moreover, bleeding (hemorrhage) can cause blood to collect and clot (hematoma). Hematomas can, for example, occur beneath the outermost of three membranes that cover the brain (meninges) as a result of a head injury. There are two types of cranial subdural hematomas. An acute subdural hematoma occurs soon after a severe head injury. A chronic subdural hematoma is a complication that may develop weeks after a head injury. Such a head injury may have been so minor that the patient does not remember it. An epidural hematoma is a traumatic accumulation of blood between the inner table of the skull and the stripped-off dural membrane. The inciting event often is a focused blow to the head. It is often difficult to detect hematomas, particularly when the hematoma occurs well after the time of an injury.

In addition to accumulation of body fluids, elevated fluid levels in tissue can arise as a result of introduction of a fluid into the body, for example, during an injection procedure. In that regard, in many medical diagnostic and therapeutic procedures, a physician or other person injects fluid into a patient's blood vessels. Moreover, in recent years, a number of injector-actuated syringes and powered injectors for pressurized injection of contrast medium in procedures such as angiography, computed tomography, ultrasound and NMR/MRI have been developed.

Extravasation or infiltration is the accidental infusion of leakage of an injection fluid such as a contrast medium or a therapeutic agent into tissue surrounding a blood vessel rather than into the blood vessel itself. Extravasation can be caused, for example, by rupture or dissection of fragile vasculature, valve disease, inappropriate needle placement, or patient movement resulting in the infusing needle being pulled from the intended vessel or causing the needle to be pushed through the wall of the vessel. High injection pressures and/or rates of some modern procedures can increase the risk of extravasation. In computed tomography, for example, contrast injection flow rates can be in the range of 0.1 to 10 ml/s.

Extravasation can cause serious injury to patients. In that regard, certain injection fluids such as contrast media or chemotherapy drugs can be toxic to tissue. It is, therefore, very important when performing fluid injections to detect extravasation as soon as possible and discontinue the injection upon detection.

Several extravasation detection techniques are known in the art. Two simple and very useful techniques for detecting extravasation are palpation of the patient in the vicinity of the injection site and simple visual observation of the vicinity of the injection site by a trained health care provider. In the palpation technique, the health care provider manually senses swelling of tissue near the injection site resulting from extravasation. By visual observation, it is also sometimes possible to observe directly any swelling of the skin in the vicinity of an injection site resulting from extravasation.

In addition to palpation and observation, there are a number of automated methods of detecting extravasation that may include automatic triggering of an alarm condition upon detection. Unfortunately, each of these automated methods of detecting extravasation is limited by significant drawbacks.

In that regard, several plethysmographic detection techniques are available. For example, mercury strain gauge plethysmographs measure the volume change resulting from venous blood flow in a cross sectional area of a limb of a patient. Air cuff or pulse volume recorder plethysmographs measure the changes in pressure within a recording cuff. Such plethysmographs can be cumbersome to operate and/or insensitive to small changes in volume.

Impedance plethysmographs use low-frequency electromagnetic energy transmitted via galvanic contact with the skin to measure changes in the electrical impedance in a defined tissue volume of a limb. Detection of extravasation via impedance changes is disclosed, for example, in U.S. Pat. Nos. 5,964,703 and 5,947,910. In this method, an impedance change of a certain level relative to a baseline measurement in the vicinity of the injection site is interpreted as being an extravasation. A change in impedance occurs during extravasation because injection fluid in the tissue of the patient changes both the volume and the electrical impedance properties of the tissue. Use of electrodes in impedance plethysmographs can, however, result in instabilities. For example, maintaining suitable electrical (ohmic or galvanic) contact between the electrodes of impedance plethysmographs and the skin of the patient is often very difficult.

Photo-plethysmographs measure the optical scattering properties of capillary blood to detect the presence of extravasated fluids in tissue. An example of a photo-plethysmograph is described in U.S. Pat. No. 4,877,034. Because light is heavily absorbed in tissue, however, the sensitivity of photo-plethysmographs is generally limited to the top ¼ inch of tissue. Many extravasations, however, occur deeper than ¼ inch. Moreover, the injection medium may flow into interstitial spaces remote from the photoplethysmograph sensors and go undetected.

A number of extravasation detection devices attempt to measure temperature differences to determine if an extravasation has occurred. For example, U.S. Pat. No. 4,647,281 discloses subcutaneous temperature sensing of extravasation to trigger an alarm. In this method of extravasation detection, an antenna and a microwave radiometer instantaneously measure the temperature of the subcutaneous tissue at the site where fluid is injected by measuring microwave radiation emitted naturally from the body. An algorithm periodically determines the temperature difference between tissue and injected fluid, and compares the difference to a fixed threshold. An alarm processor uses the comparison to determine an alarm condition.

In addition, U.S. Pat. No. 5,334,141 discloses a microwave extravasation detection system employing a reusable microwave antenna and a disposable attachment element for releasably securing the microwave antenna to a patient's skin over an injection site. The attachment element holds the antenna in intimate contact with the patient's skin to optimize microwave transfer therebetween, while shielding the antenna from environmental noise signals. U.S. Pat. No. 5,954,668 also discloses use of a microwave antenna to sense temperature of tissue to detect extravasation. Although measurement of temperature changes and emissivity using microwave energy can result in instantaneous detection, temperature differences are often too small for practical measurement.

In addition to microwave radiometry for the detection of extravasation as described above, radiometry has also been proposed for the detection of pulmonary edema as described in U.S. Pat. No. 4,488,559. U.S. Pat. No. 4,240,445 discloses detection of pulmonary edema via transmitting electromagnetic energy through a transmission line coupled to tissue. U.S. Pat. No. 4,690,149 discloses detection of brain edema via impedance changes detected by a sensor. A proposed method of detection of brain edema is also disclosed in U.S. Pat. No. 6,233,479, in which a measured signal from a microwave antenna is compared to a stored characteristic edema signal.

Microwave energy has also been used for the detection of tumors in living tissue as described in U.S. Pat. No. 6,061,589. Unlike the passive measurements in microwave radiometry, U.S. Pat. No. 6,061,589 disclosed transmission of electromagnetic energy into the body (breast tissue) using a microwave antenna in and a resultant signal is measured. In that regard, U.S. Pat. No. 6,061,589 describes a microwave antenna to detect incipient tumors in accordance with differences in relative dielectric characteristics. Electromagnetic energy in the microwave frequency range is, applied to a discrete volume in the tissue and scattered signal returns are collected. The irradiated location is shifted or changed in a predetermined scanning pattern. The returned signals are processed to detect anomalies indicative of the present of a tumor.

Microwave energy has also been used as in non-invasive tomographic spectroscopy imaging. See U.S. Pat. Nos. 6,332,087 and 6,026,173. Microwave energy has further been used to measure the fat content in nonliving organic tissue. For example, M. Kent, "Hand Held Fat/Water Determination", (1993), available at www.distell.com/products/papers/paper2.htm, discloses a microstrip sensor for such a determination. In general, the fat content of pelagic and other fatty species of fish is proportion to water content. The dielectric properties of the fish depend on the water content. In the device of Kent, changes in transmission properties of the fish were calibrated against water content.

It is desirable to develop improved devices, systems and methods for detecting changes in fluid levels in tissue, and particularly, for detecting elevated or otherwise abnormal levels of fluids in living tissue (for example, as a result of edema, hematoma or extravasation). The objectives and advantages of the invention herein presented will become fully apparent to persons skilled in the relevant art from a reading of the detailed description section of this document, and will become particularly apparent when the detailed description is considered along with the drawings and claims presented herein.

SUMMARY OF THE INVENTION

The objectives and advantages of the invention are attained by the various embodiments and related aspects of the invention summarized below.

In one aspect, the present invention provides a sensor device for detecting a change in the level of fluid within tissue of a body including: a housing having a plurality of bridge segments, the bridge segments connecting at intersections and being arranged to circumscribe an opening defined by the housing; and a plurality of antenna elements at least partially seated within the housing at intersections of the bridge segments. Each of the plurality of antenna elements includes a generally planar antenna mounted to a substrate material at a base of the planar antenna. An outer surface of the planar antenna faces away from the substrate. Each of the plurality of antenna elements further includes an electrical shield surrounding the substrate.

In one embodiment, the sensor device further includes an RF cable assembly for each of the antenna elements. Each of the RF cable assemblies includes at one end thereof a connector. At the other end thereof, the RF cable assembly is electrically connected to the antenna element corresponding thereto. The sensor device can additionally or alternatively include at least one flexible circuit board assembly for transmission of energy to and from the antenna elements. The flexible circuit board can include at least one splitter such that electromagnetic energy can be transmitted to at least two of the plurality of antenna elements using a single transmission trace within the flexible circuit board. The flexible circuit board can include at least one combiner such that electromagnetic energy can be received from at least two of the plurality of antenna elements and carried by a single transmission trace within the flexible circuit board.

The sensor device can further include an attachment mechanism to operably attach the sensor device to the tissue of the body. The attachment mechanism can include an adhesive portion defining a cutout region generally coextensive with the opening of the housing. The adhesive portion has one side thereof coated with a first adhesive adapted to removably attach to the tissue and an opposite side thereof coated with a second adhesive adapted to attach to a bottom surface of the housing. The attachment mechanism can further include a release band affixed to a perimeter of the adhesive portion. In one embodiment, the first adhesive is adapted to facilitate removal of the attachment mechanism from the patient. For example, the first adhesive can provide less adhesion than the second adhesive.

In one embodiment, each of the plurality of antenna elements of the sensor device includes at least a first antenna element pair and a second antenna element pair. The first antenna element pair includes a first transmitting antenna element and a first receiving antenna element. Likewise, the second antenna element pair includes a second transmitting antenna element and a second receiving antenna element.

The first antenna element pair and the second antenna element pair can be spaced from each other to create an area of reduced sensitivity between the first antenna element pair and the second antenna element pair. The space between the first antenna element pair and the second antenna element pair can be set so that the sensor is insensitive to fluid changes of a predetermined volume within the area of reduces sensitivity. A first area of higher sensitivity can be defined by the area between the first transmitting antenna element and the first receiving antenna element. A second area of higher sensitivity can be defined by the area between the second transmitting antenna element and the second receiving antenna element.

In another aspect, the present invention provides a sensor for detecting a change in the level of fluid within tissue of a body including a first antenna pair including a first transmitting antenna and a first receiving antenna. The first transmitting antenna is spaced from and connected to the first receiving antenna by a first bridging segment.

The sensor further includes at least a second antenna pair including a second transmitting antenna and a second receiving antenna. The second transmitting antenna is spaced from and connected to the second receiving antenna by a second bridging segment. The first antenna pair and the second antenna pair are placed in spaced connection by a first spacing segment and a second spacing segment so that an open area is defined by the first antenna pair, the second antenna pair, the first spacing segment and the second spacing segment.

Each antenna element can be surrounded by a housing section. Each of the antenna elements can include a substrate mounted within the housing section and a generally planar antenna element mounted to the substrate.

In one embodiment, the first bridging segment connects the housing section of the first transmitting antenna to the housing section of the first receiving antenna, and the second bridging segment connects the housing section of the second transmitting antenna to the housing section of the second receiving antenna. The first spacing segment can connect the housing section of the first transmitting antenna to the housing section of the second transmitting antenna, and the second spacing segment can connect the housing section of the first receiving antenna to the housing section of the second receiving antenna.

The first spacing segment and the second spacing segment can space the first antenna pair and the second antenna pair to create an area of reduced sensitivity between the first antenna pair and the second antenna pair.

In another aspect, the present invention provides a system for wirelessly communicating a change in the level of fluid within tissue of a body. The system includes: a sensor device for detecting a change in the level of fluid within the tissue; a transmitter in operative connection with the sensor device for receiving therefrom a signal indicative of the change in the level of fluid within the tissue and for transmitting a wireless signal indicative of the change in level of fluid; and a remote receiver for receiving the wireless signal transmitted by the transmitter. The remote receiver can include an indicator to provide an alert of a state determined from the received wireless signal.

In one embodiment, the sensor device can include a housing having a plurality of bridge segments, wherein the bridge segments connect at intersections and are arranged to circumscribe an opening defined by the housing. The sensor device further includes a plurality of antenna elements at least partially seated within the housing at intersections of the bridge segments. Each of the plurality of antenna elements can include a generally planar antenna mounted to a substrate material at a base of the planar antenna. An outer surface of the planar antenna faces away from the substrate. Each of the plurality of antenna elements further includes an electrical shield surrounding the substrate.

In another embodiment, the sensor device includes a first antenna pair including a first transmitting antenna and a first receiving antenna. The first transmitting antenna is spaced from and connected to the first receiving antenna by a first bridging segment. The sensor device further includes at least a second antenna pair including a second transmitting antenna and a second receiving antenna The second transmitting antenna is spaced from and connected to the second receiving antenna by a second bridging segment. The first antenna pair and the second antenna pair can be placed in spaced connection by a first spacing segment and a second spacing segment so that an open area is defined by the first antenna pair, the second antenna pair, the first spacing segment and the second spacing segment.

In a further embodiment, the sensor device includes a first antenna pair including a first transmitting antenna and a first receiving antenna The first transmitting antenna is spaced from and connected to the first receiving antenna by a first bridging segment. The sensor device further includes at least a second antenna pair including a second transmitting antenna and a second receiving antenna. The second transmitting antenna is spaced from and connected to the second receiving antenna by a second bridging segment. The first antenna pair is spaced from the second antenna pair by at least one spacing segment so that an area of reduced sensitivity is created in the space between the first antenna pair and the second antenna pair.

In another aspect, the present invention provides an attachment mechanism for use in attaching a sensing device to the skin of a patient including: an adhesive portion having a first side coated with a first adhesive adapted to removably attach to the skin and a second side, opposite the first side and coated with a second adhesive adapted to attach to the sensing device; and a release band affixed to a perimeter of the adhesive portion to facilitate removal of the attachment mechanism from attachment to the skin.

The adhesive portion can, for example, define a cutout region generally coextensive with an opening defined by the sensing device. The first adhesive can be adapted to facilitate removal of the attachment mechanism from attachment to the skin. The first adhesive can, for example, provide less adhesion than said second adhesive.

In a further aspect, the present invention provides a method of sensing a change in fluid level in living tissue in a patient including: placing a first antenna pair in contact with the patient, the first antenna pair including a first transmitting antenna and a first receiving antenna; and placing a second antenna pair in contact with the patient, the second antenna pair including a second transmitting antenna and a second receiving antenna The first antenna pair and the second antenna pair are spaced when in contact with the patient to create an area of reduced sensitivity between the first antenna pair and the second antenna pair.

The space between the first antenna pair and the second antenna pair can be set so that a sensor device including the first antenna pair and the second antenna pair is insensitive to fluid changes of a predetermined volume within the area of reduced sensitivity. A first area of higher sensitivity can be defined by the area between the first transmitting antenna and the first receiving antenna, and a second area of higher sensitivity can be defined by the area between the second transmitting antenna and the second receiving antenna.

In still a further aspect, the present invention provides a method of sensing an extravasation of fluid being injected into living tissue of a patient including: placing a first antenna pair in contact with the patient, the first antenna pair including a first transmitting antenna and a first receiving antenna;

placing a second antenna pair in contact with the patient, the second antenna pair including a second transmitting antenna and a second receiving antenna, transmitting electromagnetic energy in the frequency range of approximately 300 MHz to approximately 30 GHz via the first transmitting antenna and the second transmitting antenna; measuring resultant signals from the first receiving antenna and the second receiving antenna; and comparing the signals to a reference to determine if fluid level in the tissue has changed during the period of time. The first antenna pair and the second antenna pair are spaced when in contact with the patient to create an area of reduced sensitivity between the first antenna pair and the second antenna pair. The sensor device can, for example, include a housing that maintains the first antenna pair and the second antenna pair in spaced connection.

The space between the first antenna pair and the second antenna pair can be set so that a sensor device including the first antenna pair and the second antenna pair is insensitive to extravasations of a predetermined volume within the area of reduced sensitivity. A first area of higher sensitivity can be defined by the area between the first transmitting antenna and the first receiving antenna, and a second area of higher sensitivity can be defined by the area between the second transmitting antenna and the second receiving antenna.

In one embodiment, the frequency is in the range of approximately 1 GHz to approximately 10 GHz. In another embodiment, the frequency is in the range of approximately 3 GHz to approximately 5 GHz.

BRIEF DESCRIPTION OF THE DRAWINGS

The invention, and particularly its presently preferred and alternative embodiments and related aspects, will be better understood by reference to the detailed disclosure below and to the accompanying drawings, in which:

FIG. 1B is a bottom view of the extravasation sensor shown in FIG. 1A.

FIG. 1C is a side view of the extravasation sensor shown in FIG. 1A, with the bottom surface thereof facing towards the bottom of the page.

FIG. 1D is a top view of the extravasation sensor shown in FIG. 1A.

FIG. 1E is an end view of the extravasation sensor shown in FIG. 1A, with the bottom surface thereof facing towards the bottom of the page.

DETAILED DESCRIPTION OF THE INVENTION

Figure 1A:
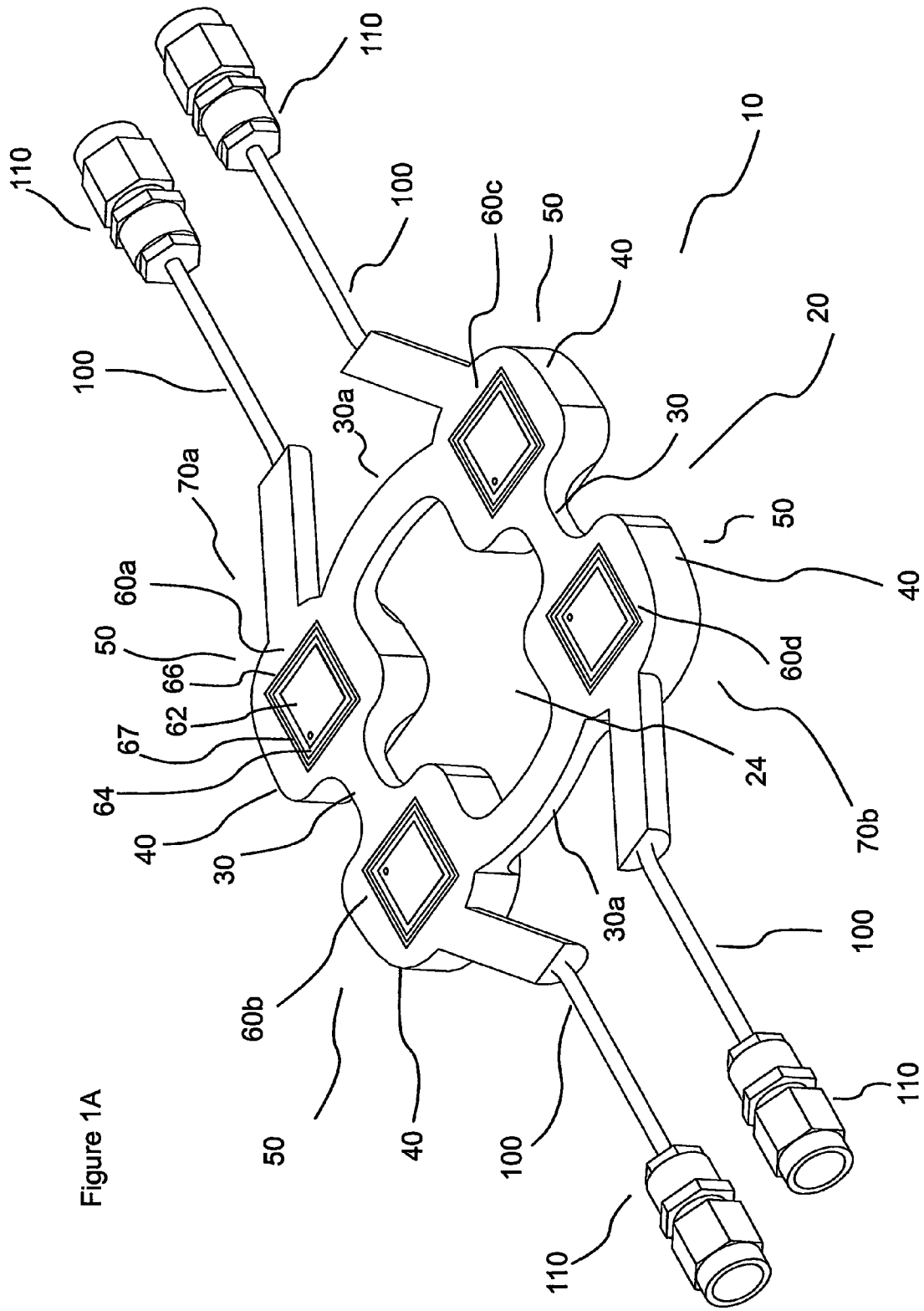
FIG. 1A illustrates a perspective view of an extravasation sensor according to a one embodiment of the present invention, showing antennae on a bottom surface thereof designed for contact with the skin of a patient and RF cable assemblies associated therewith.

While the sensors, systems and methods of the present invention are generally applicable to the sensing any fluid within body tissue (whether a body fluid or an introduced fluid), the present invention is primarily described herein with reference to the representative example of extravasation of a fluid intended to be injected into a vascular structure. One skilled in the art will appreciate, however, that elevated, abnormal or changing levels of generally any fluid can be detected using the sensors, systems and methods of the present invention. Detection of body fluids in the present invention includes, but is not limited to, the detection of fluid changes as a result of edema, hematoma, ruptured bowel and colostomy tubing leakage into the peritoneal cavity. Introduced or foreign fluid detectible in the present invention include fluid introduced via generally any technique known in the medical arts including, but not limited to, injection, infusion and IV drip. As described above, changes in complex permittivity and permeability as a result of changing fluid levels in tissue are detected by application of electromagnetic energy to the tissue and detection of a resultant signal.

Complex permittivity and permeability govern how an electromagnetic wave will propagate through a substance. Complex permittivity typically has the greatest effect since it varies significantly between tissue types and fluids of interest. The complex permeability of various tissues and many fluids of interest is approximately that of a vacuum, reducing the effect of this parameter. Some fluids, however, such as MRI contrast agents may have an appreciable complex permeability difference from tissue.

Although blood contains small amounts of iron, the permeability value for any significant volume of blood is typically insignificant. Complex permittivity is generally expressed as:

$$\in^* = \in' - j\in''$$

wherein $\in'$ is the real component of the complex value and is known as the dielectric constant or sometimes simply referred to as the "permittivity." The term $\in''$ is the imaginary component of the complex value and is often referred to as the "loss factor." The ratio of ($\in''/\in'$) is known as the "loss tangent." The complex permittivity (and sometimes permeability) of certain substances differ from the body tissue at certain frequencies. In the present invention, such differences in permittivity and/or permeability are used for the detection and level monitoring of certain fluids and substances in biological tissue.

Published U.S. Patent Application Publication Nos. 2003/0036674 and 2003/0036713, assigned to the assignee of the present invention, the disclosures of which are incorporated herein by reference, disclose transmitting and receive antenna elements, sensing methods and processing algorithms suitable for use in the present invention. The studies of sensors incorporating such antenna elements have shown that electromagnetic energy having, for example, a frequency in the range of approximately 300 MHz to approximately 30 GHz (and, more preferably, in the range of approximately 1 GHz to approximately 10 GHz, and, even more preferably, in the range of approximately 3 GHz to approximately 5 GHz) provides good penetration into tissue. In general, such electromagnetic energy is launched into the subcutaneous tissue and a resultant signal is measured. Electromagnetic energy in the frequency range set forth above has been found to transmit through the skin and to transmit or propagate well within, for example, fat. Good transmission through the fat layer is beneficial for detection of extravasation as many extravasations occur in the fat layer. The sensitivity to extravasation of the systems, devices and methods of the present invention is thus increased as compared, for example, to impedance plethysmography.

FIG. 1A-1E illustrate multiple views of one embodiment of an extravasation sensor 10 of the present invention. Extravasation sensor 10 includes a housing 20, a plurality of antenna or sensor elements 60a, 60b 60c and 60d, and the RF cable assemblies 100 associated therewith. Each of coaxial cables 100 includes a subminiature coaxial connector (SMA connector) 110.

The housing 20 can, for example, be fabricated from a base material, such as urethane and/or silicone material. A ferromagnetic and/or other material suitable to absorb leakage of electromagnetic energy can be mixed into the base material. A carbonyl iron powder, such as the EW grade carbonyl iron powder produced by the BASF Corporation, of Mount Olive, N.J., is suitable for this purpose. The ferromagnetic powder is mixed into the housing base material at least around the antenna elements and cables. A ferromagnetic material with appreciable permeability (e.g., >1), such as the EW grade carbonyl iron powder, provides a mixture that creates a flexible housing capable of absorbing stray leakage of electromagnetic energy. If not effectively addressed, such leakage could potentially cause artifacts to be induced within the signals conveyed from the antenna elements 30 as a result of, for example, palpation of the skin in the area of the extravasation sensor 10 or as a result of other movement of the sensor 10. In addition to motion and palpation artifacts, such leakage could also decrease the sensitivity of the sensor 10 to the presence of subcutaneous fluid. It is apparent that one can also mix the ferromagnetic material into a different base material (for example, a base material that will form a more rigid housing).

As illustrated, for example, in FIGS. 1A-1E and 2, housing 20 of the extravasation sensor 10 defines an opening 24 between the antenna elements 60a-d. Opening 24 provides both visual and tactile (palpation) access to the site of interest where subcutaneous fluid will likely accumulate should extravasation occur. Opening 24 thus provides the operator with the option of checking for or confirming the presence of fluid merely by looking at or palpating the skin through opening 24 in housing 20.

Housing 20 also includes segments 30 and 30a that bridge the gap between seatings 40 (positioned at intersections 50 between connected segments 30 and 30a) in which antenna elements 60a-d are seated. Bridge segments 30 and 30a are, for example, low in profile to provide an operator access through opening 24 to the site of interest for the purpose of palpation. Nurses or technologists often position their hand in such a manner that low-profile bridge segments 30 and 30a (particularly those bridge segments 30a on the sides of sensor 10) allow improved ability to palpate the site of interest to check for extravasation. As best shown in FIGS. 1A and 1C, side bridge segments 30a can be curved outwardly away from the center of the palpation area to allow increased accessibility.

Similar to the antenna element described in Published U.S. Patent Application Nos. 2003/0036674 and 2003/0036713, antenna elements 60a-d (each of which is generally identical in structure), in several embodiments of the present invention, include an active antenna or resonant structure 62 surrounded by a substrate 64 such as a ceramic material (for example, $MgCaTiO_2$). Resonant structures 62 are, for example, adapted to transmit and receive electromagnetic energy in the frequency ranges set forth above. The substrate material can, for example, have a moderate to high dielectric constant (for example, in the range of approximately 5 to approximately 100 or in the range of approximately 50 to approximately 80) or high permittivity and low loss. To reduce the size of the antenna structure, several embodiments used in the studies of the present invention used a ceramic material in the range of 5-15, thereby reducing manufacturing costs The impedance of substrate 64 is preferably similar to that of the surface of the tissue to be studied.

Unlike several of the embodiments of the antenna elements of U.S. Patent Application Nos. 2003/0036674 and 2003/0036713, antenna elements 60a-d of the present invention did not include a superstrate material. In U.S. Patent Application Publication Nos. 2003/0036674 and 2003/0036713, the antenna elements such as shown in FIG. 7D of each of those published U.S. patent applications were positioned atop or otherwise formed within a substrate and shielded from direct contact with the skin by use of a superstrate. By forming antenna elements 60a-d without a superstrate, antenna element 60a-d becomes electromagnetically loaded when adjacent to human tissue on which extravasation sensor 10 is positioned. This electromagnetic loading increases the bandwidth of extravasation sensor 10, which increases its ability to detect subcutaneous pools of various shapes and sizes.

Microstrip antennae 60a through 60d used in several studies of the present invention were fabricated from a ceramic laminate material coated with thin layers of copper on the front and back thereof. Such a material is, for example, available from Rogers Corporation of Chandler, Ariz. under the product name RT/duroid® 6010LM. Such microwave laminates are ceramic-PTFE composites designed for electronic and microwave circuit applications requiring a relatively high dielectric constant.

RT/duroid 6010LM laminate has a dielectric constant of approximately 10.2. The laminate was approximately 2.5 mm thick and was supplied with both sides thereof clad with ¼ to 2 oz./ft.$^2$ (8 to 70 µm) electrodeposited copper foil. In fabricating antennae (or microstrip antennae) 60a-d of the present invention, some of the copper material was etched from the top of the laminate to form generally planar antenna active element or resonant structure 62, thereby forming a margin between the outer edge of resonant structure 62 and the outer edge of substrate 64. The copper on the bottom side of the laminate formed ground plane 66 of antenna 62a-d. Side shielding 68 of a conductive material can be provided to, for example, improve tissue coupling and prevent stray energy.

Side shielding 68 and rearward, ground plane 66 form an electrically conductive cavity. Resonant structure 62 and the cavity can resonate together in the frequency range of interest. Such resonance matching can improve efficiency by, for example, increasing power output relative to power input for transmission, and increasing power received relative to power available for reception. Each antenna element 60a through 60d can also include a conductive front lip 67 on the surface of the ceramic material to provide additional shielding.

Coupled with the protection provided by the side shielding 68, forward conductive lip 67 for each antenna elements 60a-d serves to further decrease the leakage of stray electromagnetic energy. In one embodiment, conductive lip 67 was fabricated from a conductive material such as copper having a thickness of approximately 0.010 inches.

Although square antennae or resonant structures 62 were used in the studies of the present invention, it is clear to one skilled in the art that many alternative antenna element or resonant structure geometries (for example, circular or rectangular) can be used in the antennae of the present invention.

Figure 2:
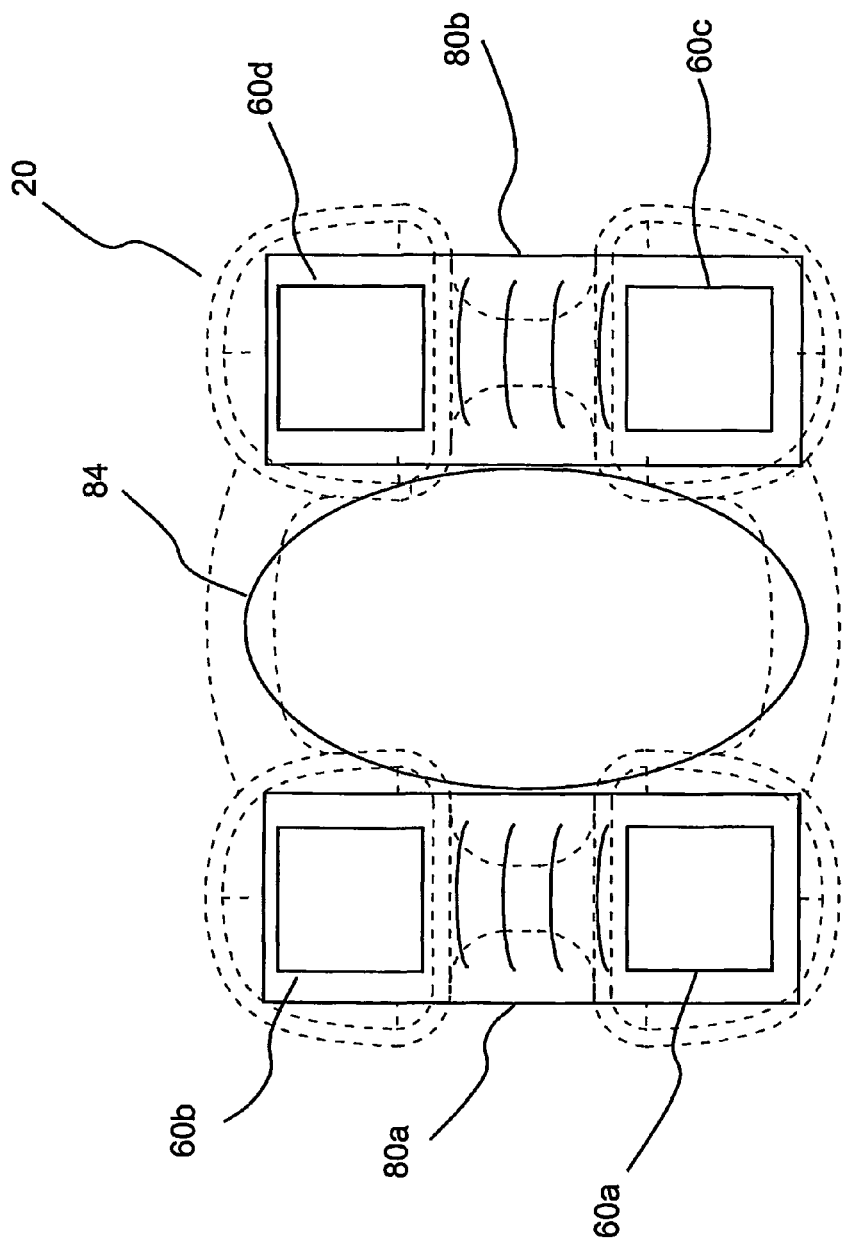
FIG. 2 illustrates a generalized and idealized structural layout of the sensor of FIG. 1A, showing high sensitivity zones and an intermediate, reduced sensitivity zone.

In the embodiment of FIGS. 1A through 2, sensor 10 includes two antenna sets or pairs 70a and 70b. First antenna pair 70a includes first transmitting antenna element 60a and first receiving antenna element 60b. Second antenna pair 70b includes second transmitting antenna element 60c and second receiving antenna element 60d. The transmitting and receiving antenna elements of each of first antenna pair 70a and second antenna pair 70b are held in spaced connection by bridging segments 30. The length of bridging segments 30, and thus the space between the transmitting and receiving antenna elements, can be used to adjust the sensitivity of the antenna pair to fluid changes in the high sensitivity zone of the sensor (see, for example, FIG. 2 and the discussion thereof below) located between the transmitting antenna and the receiving antenna of the antenna pair. In that regard, increasing the distance between the transmitting antenna and the receiving antenna increases the volume of tissue encompassed by the high sensitivity zone, but also increases the minimum volume of fluid change that can be detected.

FIG. 2 illustrates a schematic structural layout for extravasation sensor 10 of the present invention, in which four antenna elements 60a through 60d are separated to form a first high sensitivity zone 80a between antenna elements 60a and 60b and a second high sensitivity zone between antenna elements 60c and 60d. Between high sensitivity zones 80a and 80b is a region or zone 84 of lower or reduce sensitivity. The size of the reduced sensitivity zone 84 (and the sensitivity therein) is determined by the length of side bridging segments 30a which operatively connect and space first antenna pair 70a and second antenna pair 70b. In this embodiment of the present invention, the spacing between antenna pairs 70a and 70b effectively increases the sensing range of extravasation sensor 10. However, lower sensitivity to small volumes of subcutaneous fluid in reduced sensitivity zone 84 between antenna pairs 70a and 70b is achieved by spacing antenna pairs 70a and 70b. High sensitivity zones 80a and 80b are "primary" areas in which fluid build up can be detected with highest sensitivity. The formation of intermediate, reduced sensitivity zone 84, however, allows a small, clinically insignificant amount of fluid (e.g., blood contrast agent, or saline) to collect before extravasation sensor 10 indicates a positive response. This configuration can be particularly desirable in, for example, the computerized tomography (CT) setting wherein extravasation of a small amount of fluid happens in a percentage of procedures and does not require the termination of the CT examination. In that regard, a study by Birnbaum et al. (Birnbaum et al., "Extravasation Detection Accessory: Clinical Evaluation in 500 Patients," *Radiology* (1999)) noted an occurrence rate of 2.6% for small leaks of contrast agent at the tip of the catheter with a volume range of such leaks of approximately 0.5 to 3 cc. During an injection procedure, sensor 10 can be positioned so that the tip of the injection catheter is placed within reduced sensitivity zone 84 (for example, positioned generally centrally within reduced sensitivity zone 84 or within open area 24).

Using sensing algorithms and thresholds as disclosed in Published U.S. Patent Application Nos. 2003/0036674 and 2003/0036713, small volumes of fluid (for example, volumes no greater than 5 cc or no greater than 3 cc) can accumulate within the overall sensing region while not crossing the alarm threshold. Further, higher threshold values can be set and remain effective at desired levels (that is, clinically significant levels). Moreover, by creation of reduced sensitivity zone 84 the volume at which the overall sensing region begins to become saturated (i.e., at which fluid has filled the overall sensing region and the sensor's the signal stops changing) is increased to a larger volume by creation of reduced sensitivity zone 84.

As described above, reduced sensitivity zone 84 allows small, clinically insignificant, extravasation (blood and/or contrast agent) volumes to accumulate while significantly reducing the probability of a false positive alarm. Indeed, in several clinical studies of the present invention, false positive alarms were maintained below 0.1% while a positive extravasation detection rate in excess of 95% was achieved.

As illustrated for example in FIG. 2, reduced sensitivity zone 84 is located between high sensitivity zones or sensing areas 80a and 80b. Increased fluid levels in low sensitivity region 84 can cause tissue distortion in one or both of high sensitivity zones 80a and 80b, and indirectly cause some level of sensor response. Because of such effective overlap of high sensitivity zones 80a and 80b and intermediate, reduced sensitivity zone 84, the overall fluid volume sensing range of sensor 10 is increased significantly.

In addition to maintaining a predetermined, desired spacing between the antenna elements of each antenna element pair and a predetermined, desired spacing between the antenna element pairs, housing 20 also maintains a desired relative orientation between the antenna elements of each antenna element pair and between the antenna element pairs. Also, housing 20 assists in assuring that each of antenna elements 60a-d is generally coplanar when sensor device 10 is in operative connection with a patient's skin.

Figure 3:
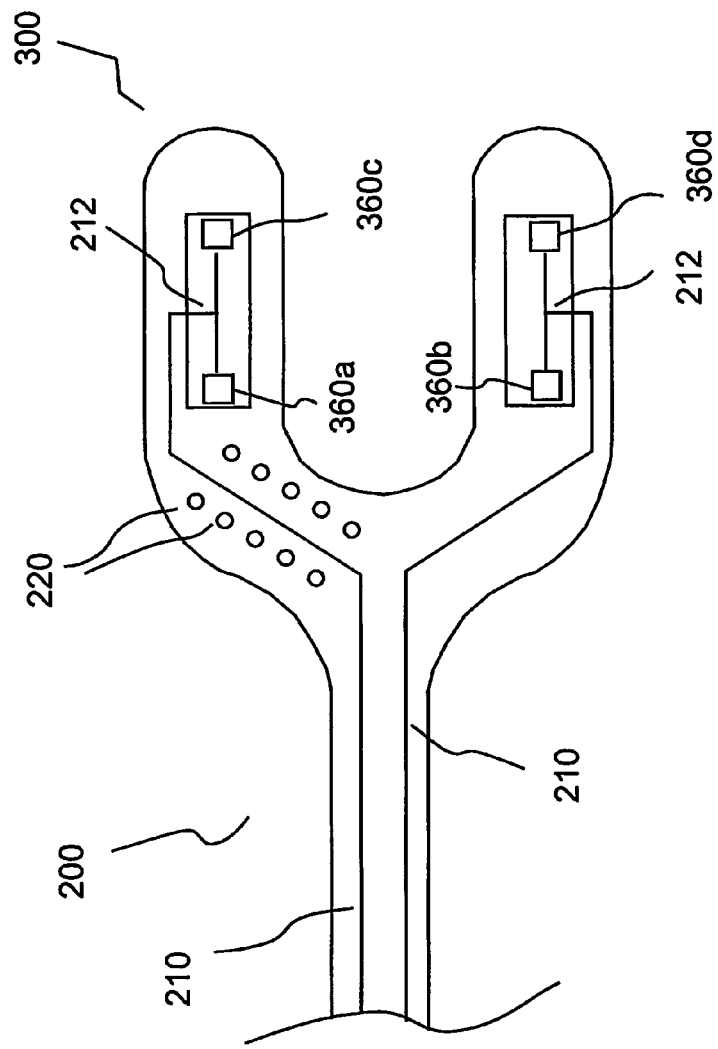
FIG. 3 depicts an embodiment of a layout for a flexible circuit board, showing flexible striplines for use in conveying signals to and from the antennae of an extravasation sensor such as the one shown in FIG. 1A.

FIG. 3 illustrates an embodiment of use of a flexible circuit board (also referred to as a "RF flex circuit board") to create a unique thin, "flexible strip" or flexible circuit transmission system 200 that can be used to carry and distribute the electromagnetic (for example, microwave) signals being transmitted from and received by extravasation sensor 300. Sensor 300 includes antenna elements 360a-d which operate in a manner as described above in connection with antenna elements 60a-d. Flexible strip transmission system 200 includes transmission lines or traces 210. The flexible strip transmission system 200 is provided with "side vias" 220 which (in connection with conductive layers laminated on the major surfaces of the flexible strip) complete a shielded, fall coaxial structure for use in carrying microwave signals to and from antenna elements 360a-d of sensor 300. In that regard, top and bottom conductive layers of flexible strip transmission system 200 serve as ground planes, while vias between those layers are used to provide side shielding. As shown in FIG. 3, traces 210 can, for example, include splitting and combining geometries 212 to split the energy between multiple transmitting antenna elements such as antenna elements 260a and 260c and to combine energy from multiple receiving antenna elements such as antenna elements 260b and 260d if desired. This splitting and combining allows the use of fewer cables when connecting sensor 300 to processing circuitry. Flex circuit boards and other materials suitable for use at microwave frequencies are commercially available from, for example, DuPont and the Advanced Circuit Materials Division of Rogers Corporation, of Chandler, Ariz.

A further advantage of the use of flex circuit board in connection with an energy transmission system of the sensors of the present invention is that a low-profile connection to the antennas elements can be achieved. Use of coaxial cables which are soldered to the antennas elements of the present invention can require a sizeable bending radius, creating a higher profile connection. RF flex circuit includes an RF vertical transition including a center signal via surrounded by ground/reference vias completing a coaxial structure to transmit/receive microwave energy to and from the antennas elements. The antenna elements can, for example, be wave soldered in an automated process directly to the thin RF flex circuit without use of additional connectors or cables, achieving a low-profile connection.

By using thin dielectric layers in the flex circuit boards of the present invention and designing appropriate signal traces in the signal plane, small changes in the gain and phase characteristics during, for example, bending and twisting of the RF flex circuit were achieved. These results can reduce effects, if any, of motion artifact during sensor use.

Figure 4:
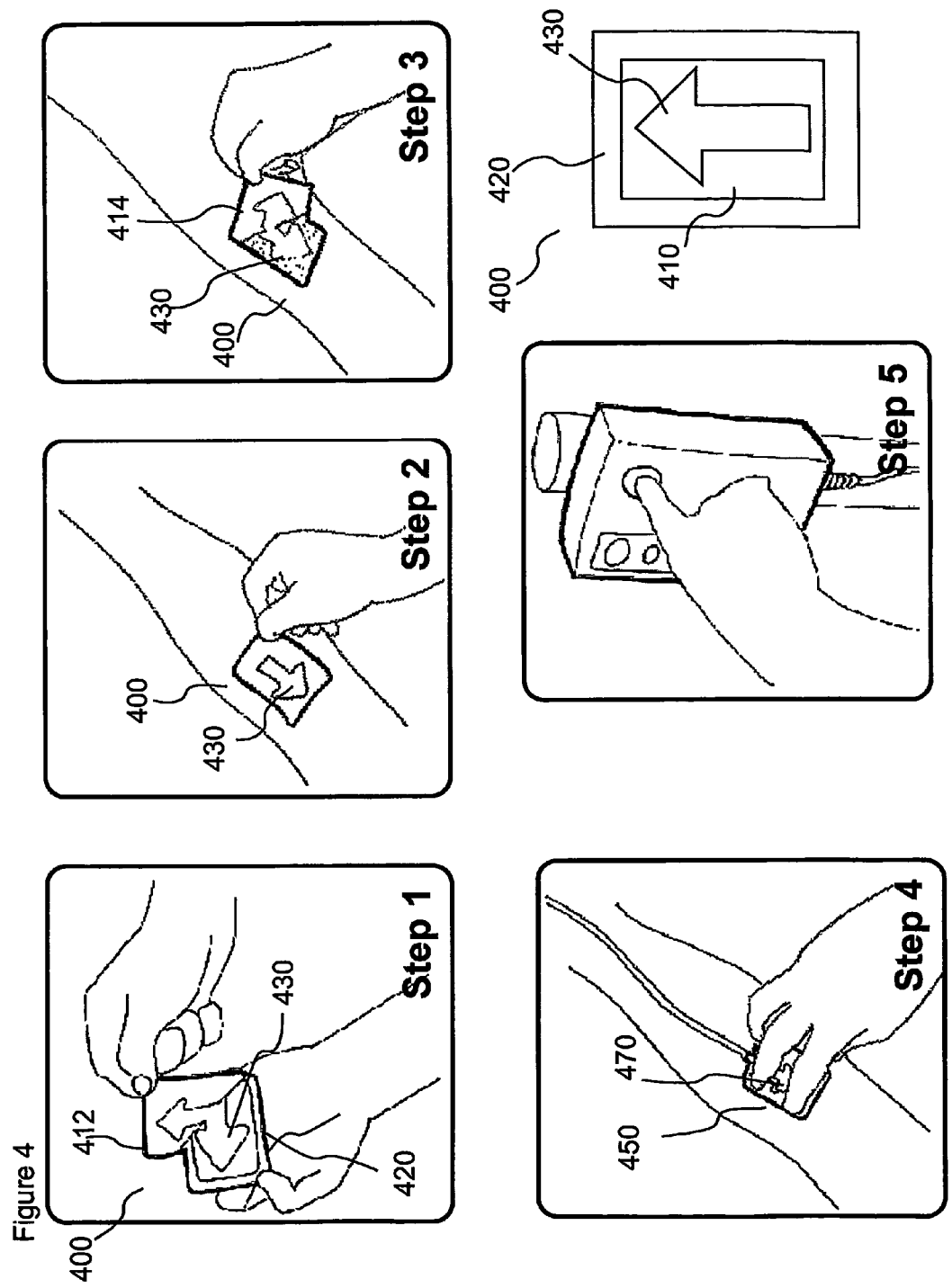
FIG. 4 illustrates a step-by-step procedure for using an attachment mechanism to attach an extravasation sensor of the present invention to the skin of a patient.

FIG. 4 illustrates one embodiment of a step-by-step procedure for using an attachment mechanism 400 of the present invention to attach an extravasation sensor 450 of the present invention to the skin of a patient. Designed to be disposable, attachment mechanism 400 includes a double-sided adhesive portion 410 and a release band 420 (which preferably includes no adhesive) around the perimeter of adhesive portion 410. In addition, adhesive portion 410 defines a cutout region 430. Cutout region 430 can be shaped in the shape of an arrow (pointing, for example, in the direction of contrast medium flow) or other shape to indicate a preferred orientation for attachment. One side of double-sided adhesive portion 410 is designed to attach to the skin of the patient over the site or region of interest (typically centralized on the tip of the catheter), and the opposite side is designed to permit extravasation sensor 450 to be affixed thereto. When properly applied, cutout region 430 of adhesive portion 420 and an opening 470 of extravasation sensor 450 are generally coextensive, thereby allowing the operator visual and tactile (palpation) access to the site of interest.

As illustrated in FIG. 4, in a first step an operator removes a first cover film or layer 412 from the side of double-sided adhesive portion 410 including the adhesive adapted to attach to the patient's skin. In step 2, attachment mechanism 400 is attached to the patient skin with the arrow of cutout portion 430 pointing in the direction of the contrast medium flow. In step 3, a second cover film or layer 414 is removed from the side of double-sided adhesive portion 410 including the adhesive adapted to attach sensor 450 to attachment mechanism 400. In step 4, sensor 450 is attached to the attachment mechanism 400 so that open area 470 of sensor 450 is in general alignment with cutout region 430. In step 5, the sensing module is armed.

Figure 5:
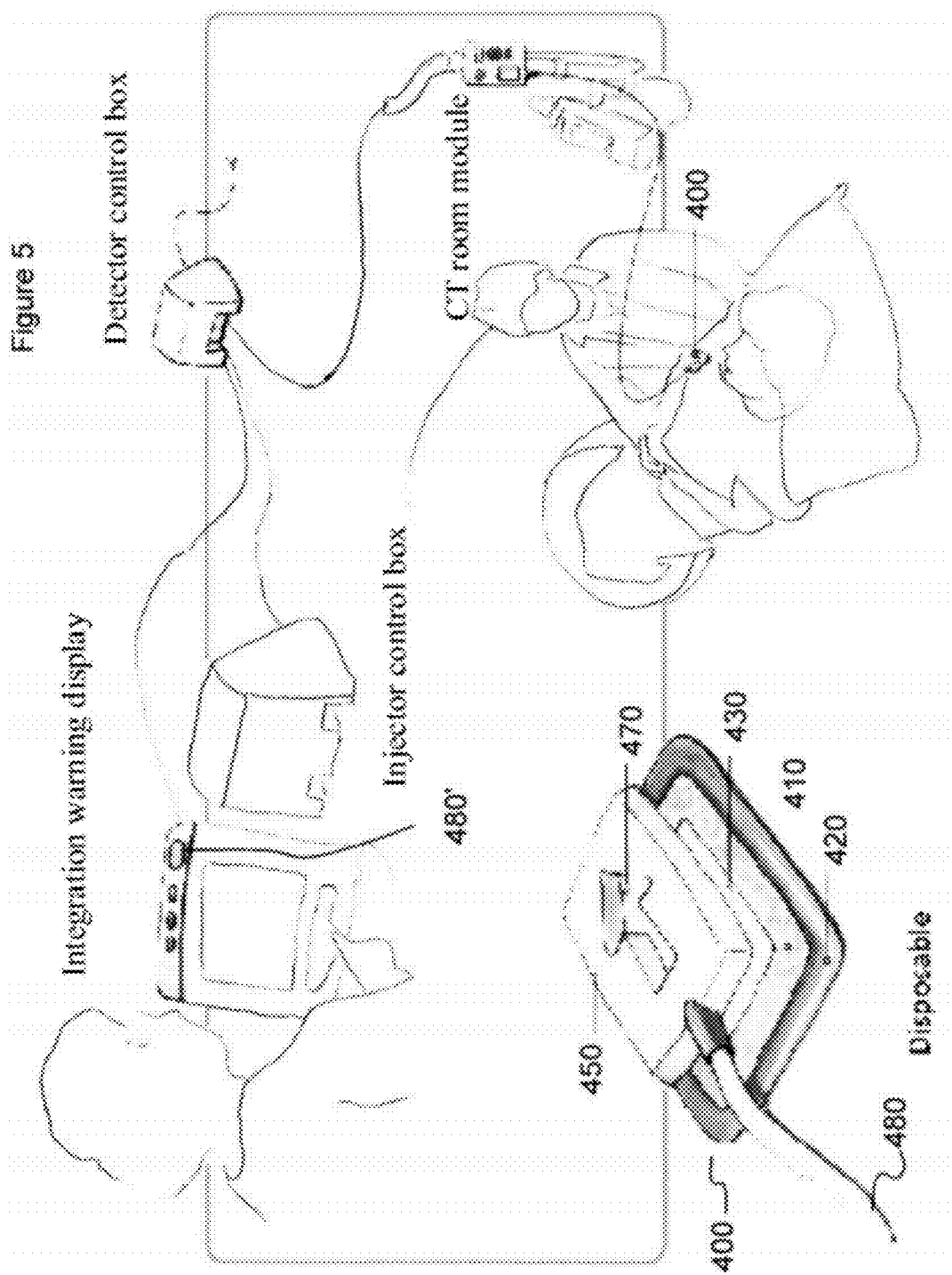
FIG. 5 illustrates an extravasation sensor attached to the patient via the attachment mechanism of FIG. 4 and its use within a control room of an imaging suite.

As illustrated, for example, in FIG. 5, release band 420 of attachment mechanism 400 enables the operator to pull attachment mechanism 400 off the skin after use of extravasation sensor 450 is complete. For ease of use, the color, material or texture of adhesive portion 410 and release band 420 can be different. This difference facilitates the positioning and secure attachment of extravasation sensor 450. Each side of attachment mechanism 400 can have a different level of adhesion (i.e., aggressiveness of adhesive) which facilitates the tailoring of the adhesion to the skin side which may be less than that of the sensor side.

In several studies of the attachment mechanisms of the present invention, 3M Medical Double Coated Tape #1512 available from 3M of Saint Paul, Minn. was used. This tape is fabricated from a hypoallergenic polyethylene material. Whatever double-sided adhesive tape or film is used, the double-sided adhesive tape preferably maintains sufficient contact with the skin and (upon proper use) provides resistance to wrinkling and formation of air pockets upon placement. The double-sided adhesive tape material preferably has a low electromagnetic loss factor (that is, in the sensor's operating frequency range). Such properties allow the electromagnetic energy (for example, microwaves) to penetrate the adhesive tape effectively. Most adhesive tapes possess these characteristics. Tapes that contain metallic particles or other conductive materials, however, may not be suitable for use in the attachment mechanisms of the present invention. The tape can, however, contain, for example, a material such as a ceramic material that yields a thin structure with low electromagnetic loss and an impedance that matches the surface tissue. This embodiment can provide better coupling of the microwave energy between the antennas and the tissue to increase detection sensitivity while decreasing leaked energy and thereby decreasing any palpation/motion artifact.

As an alternative to the steps described in connection with FIG. 4, one can first adhere the double-sided tape to the sensor face while applying pressure with fingers across the entire sensor contact/antenna faces (ensuring good adhesion and prevention of air pockets). The inner or patient side cover film 412 is the removed and the attachment mechanism/sensor assembly is placed against the skin, briefly applying pressure.

Figure 6:
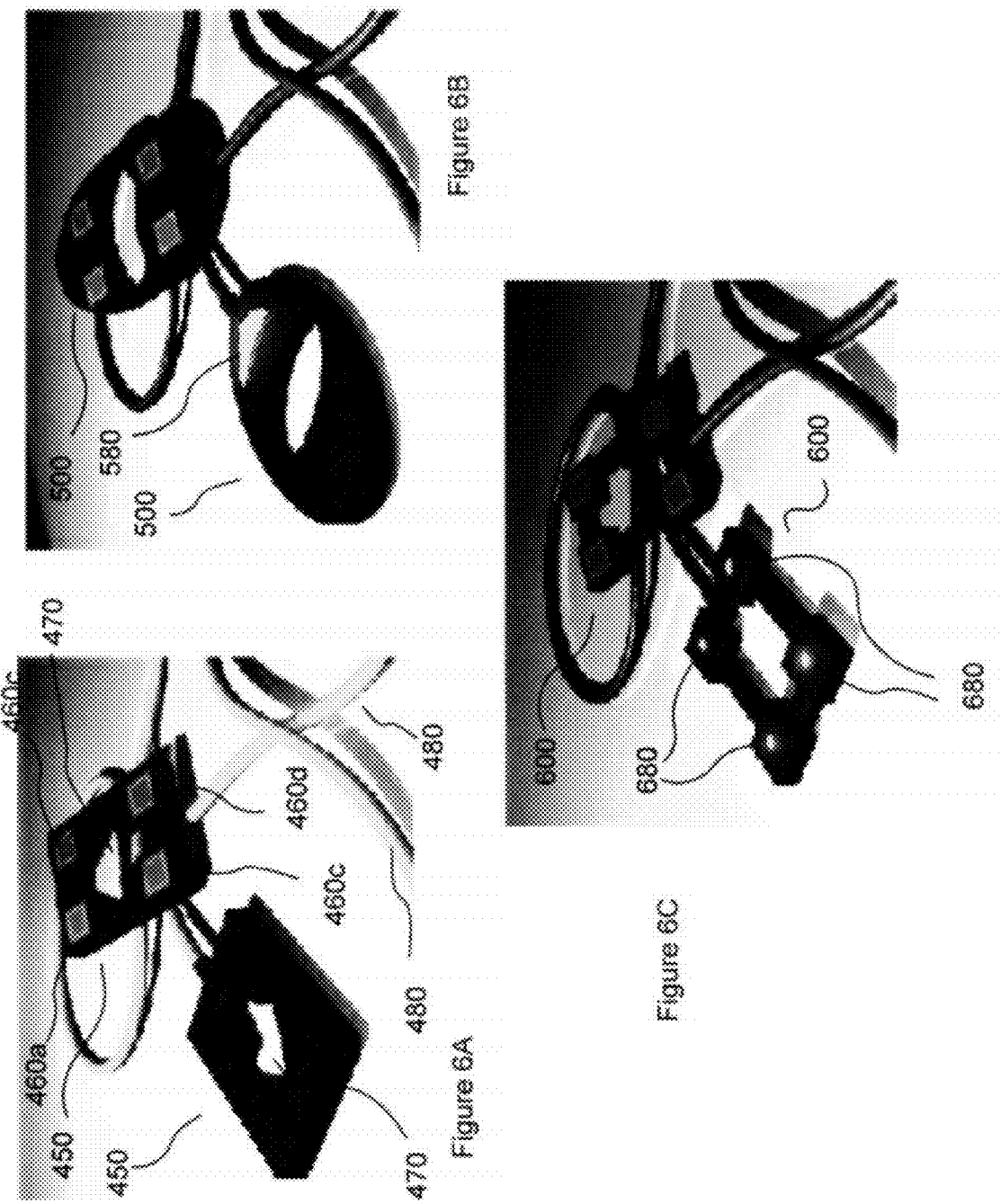
FIG. 6A illustrates an extravasation sensor according to the present invention including one or more indicators to provide a visual indication of extravasation.
FIG. 6B illustrates an extravasation sensor according to the present invention into which an arm button has been incorporated and which doubles as a visual indicator of extravasation.
FIG. 6C illustrates an extravasation sensor according to the present invention into which an indicator has been incorporated into each antenna element as a visual indicator of extravasation.

As shown in FIGS. 4, 5 and 6A, and as described above, opening 470 for palpation in the housing of extravasation sensor 400 as well as the cutout region of the attachment mechanism can be formed to indicate the direction to which the sensor should be placed (e.g., arrow shaped). This shape of opening 470 also helps the operator to align extravasation sensor 450 and attachment mechanism 400 for optimal attachment to a patient's skin, which is important for integrity of the signals detected and conveyed by extravasation sensor 400.

Extravasation sensor 450 and other extravasation sensors of the present invention can also be equipped with one or more user interfaces or indicator. FIGS. 6A and 6B, respectively, illustrate that a light pipe 480 or other visual indicators, such as light-emitting diodes 580 (LEDs) on sensor 500, can be incorporated into the extravasation sensors of the present invention to provide, for example, a visual indication of extravasation. Additional or alternatively, other types of indicators such as audible indicators or tactile indicators can be provided. In FIG. 6A, a light pipe 480 is incorporated into the RF cable assembly that interconnects the extravasation sensor and its associated base/control unit so that the entire cable or a portion thereof lights to indicate a positive extravasation state. A light pipe can also pass through the cabling to light an indicator on the housing of the sensor. In FIG. 6C, a plurality of indicator lights 580 are provided. Furthermore, a user input button for functions such as "arming" or "baselining" the overall system can be implemented at the extravasation sensor of the present invention. In FIG. 6B, indicator 580 is also a user input button. An audible, tactile and/or visual alarm can also be integrated within the housing of the sensor. These features are advantageous because the user often focuses on the injection site (in CT application, for example) and therefore will not only more readily observe the light indicators situated there but also be more readily disposed to provide input from there.

An indicator device such as indicator light 480' can alternatively or additionally be mounted to or otherwise integrated into a remote display or controller unit for the injector system, as, for example, illustrated in FIG. 5 in the context of a CT imaging suite. Such a remote display or control unit is typically located in the control room of a CT suite rather than in the scanner room where the injector and extravasation sensor will be sited.

Figure 7:
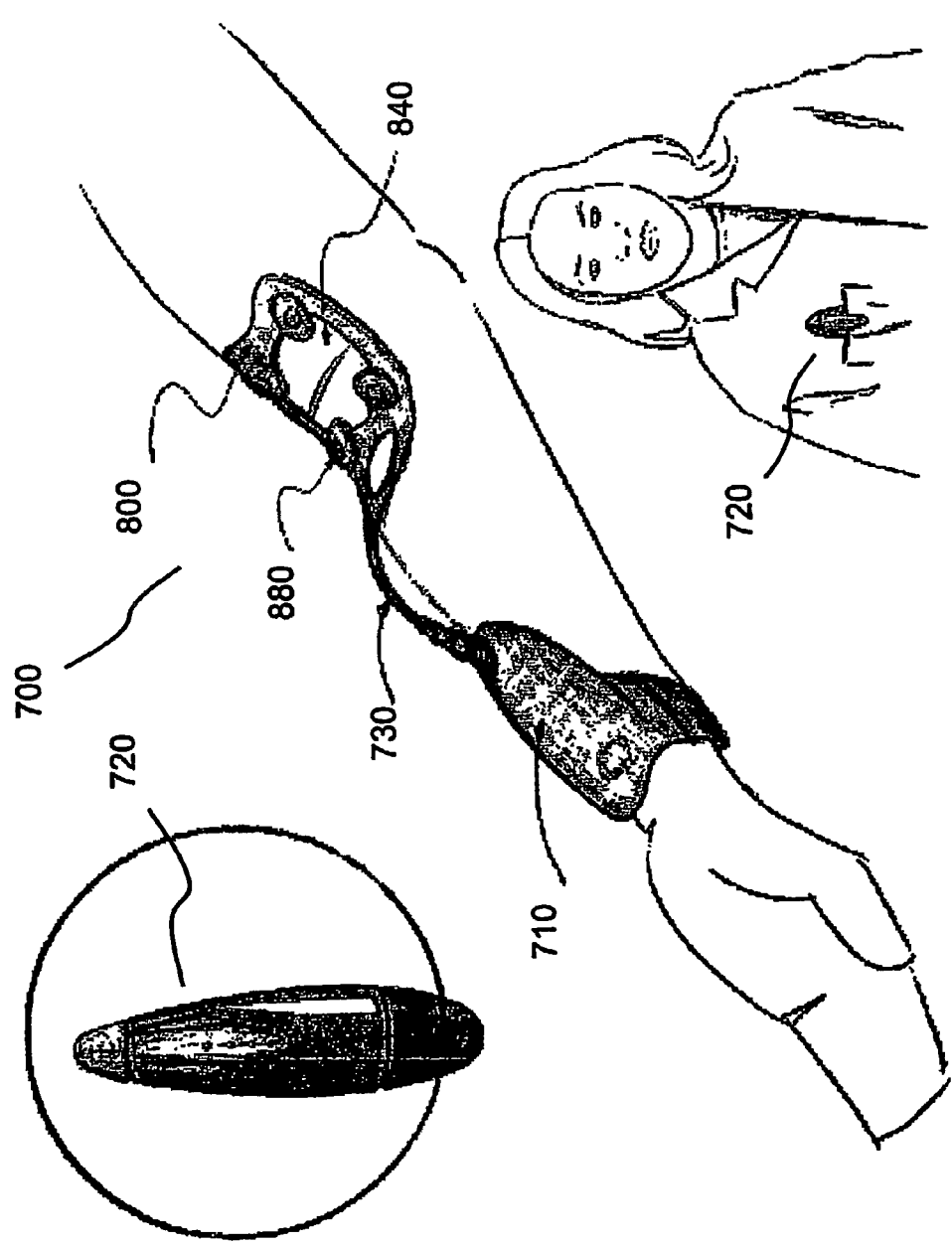
FIG. 7 illustrates a system for wirelessly transmitting a signal indicative of extravasation from an extravasation sensor (such as the one shown in FIG. 1A) to a remote receiver.

FIG. 7 illustrates a system 700 for wirelessly transmitting a signal indicative of extravasation from an extravasation sensor 800 outfitted with a transmitter 710 (for example, an RF transmitter) to a remote receiver 720. Such a wireless system 700 can be implemented with any extravasation sensor of the present invention. In one embodiment, wireless system 700 includes a short RF cable 730 connecting sensor 800 to transmitter 710. In use, extravasation sensor 800 can be attached to, for example, the upper arm about the site of the injection and transmitter 710 can be strapped or otherwise attached near or directly to the wrist. If extravasation sensor 800 is attached to the back of the hand or wrist, RF transmitter 710 can then be strapped to the upper arm much like a sports radio. Short RF cable 730 interconnects the two components as described above, and can be either a distinct component or emanate from the housing of sensor 800. Short RF cable 730 in this configuration can improve performance and decrease the potential of motion artifacts and other complications that may be associated with certain longer cables. In the embodiment of FIG. 7, sensor 800 includes a palpation opening 840 and indicator lights 880 which operate as described above.

Although the various embodiments and related aspects of the invention herein described and illustrated are presented primarily in the context of CT imaging procedures, one skilled in the art understands that the invention may also be applied or adapted to other types of applications such as positron emission tomography (PET), magnetic resonance imaging (MRI), magnetic resonance angiography (MRA) and ultrasound procedures as well as a wide variety of therapeutic and other procedures.

The presently preferred embodiment(s) for carrying out the invention have been set forth in detail according to the Patent Act. Persons of ordinary skill in the art to which this invention pertains may nevertheless recognize alternative ways of practicing the invention without departing from the concepts and embodiments disclosed herein.

What is claimed is:

1. A sensor device for detecting a change in the level of fluid within tissue of a body, the sensor device comprising:
    a housing having a plurality of bridge segments, the bridge segments connecting at intersections and being arranged to circumscribe an opening defined by the housing; and
    a plurality of antenna elements at least partially seated within the housing at intersections of the bridge segments, each of the plurality of antenna elements comprising a generally planar antenna mounted to a substrate material at a base of the planar antenna, an outer surface of the planar antenna facing away from the substrate, each of the plurality of antenna elements further comprising an electrical shield surrounding the substrate,
    wherein the each of the plurality of antenna elements comprises at least a first antenna element pair and a second antenna element pair, the first antenna element pair comprising a first transmitting antenna element, a first receiving antenna element, and a first bridging segment, the second antenna element pair comprising a second transmitting antenna element, a second receiving antenna element and a second bridging segment,
    wherein a first high sensitivity zone is formed between the first transmitting antenna element and the first receiving antenna element and a second high sensitivity zone is formed between the second transmitting antenna element and the second receiving antenna element
    wherein the first antenna element pair and the second antenna element pair are spaced from each other to create an area of reduced sensitivity between the first high sensitivity zone and the second high sensitivity zone,
    wherein the space between the first antenna element pair and the second antenna element pair is set so that the sensor is insensitive to fluid changes of a predetermined volume within the area of reduced sensitivity.

2. The sensor device of claim 1 further comprising an RF cable assembly for each of the antenna elements, each of the RF cable assemblies at one end thereof comprising a connector and at the other end thereof being electrically connected to the antenna element corresponding thereto.

3. The sensor device of claim 1 further comprising at least one flexible circuit board assembly for transmission of energy to and from the antenna elements.

4. The sensor device of claim 3 wherein the flexible circuit board comprises at least one splitter such that electromagnetic energy can be transmitted to at least two of the plurality of antenna elements using a single transmission trace within the flexible circuit board.

5. The sensor device of claim 3 wherein the flexible circuit board comprises at least one combiner such that electromagnetic energy can be received from at least two of the plurality of antenna elements and carried by a single transmission trace within the flexible circuit board.

6. The sensor device of claim 1 further comprising an attachment mechanism to operably attach the sensor device to the tissue of the body, the attachment mechanism comprising:
    an adhesive portion defining a cutout region generally coextensive with the opening of the housing, the adhesive portion having one side thereof coated with a first adhesive adapted to removably attach to the tissue and an opposite side thereof coated with a second adhesive adapted to attach to a bottom surface of the housing.

7. The sensor device of claim 6 wherein the attachment mechanism further comprises a release band affixed to a perimeter of the adhesive portion.

8. The sensor device of claim 7 wherein the first adhesive provides less adhesion than the second adhesive.

9. The sensor device of claim 1 wherein the electrical shield comprises a rearward section adjacent a rearward side of the substrate, side shields encompassing sides of the substrate and a forward section adjacent a forward side of the substrate and extending inward from the side shields, a margin being maintained between the planar antenna and the forward section.

10. The sensor device of claim 1 wherein the plurality of antenna elements emit electromagnetic energy in the range of approximately 300 MHz to approximately 30 GHz.

11. A sensor for detecting a change in the level of fluid within tissue of a body, comprising:
    a first antenna pair comprising a first transmitting antenna element and a first receiving antenna element, the first transmitting antenna element being spaced from and connected to the first receiving antenna element by a first bridging segment; and
    at least a second antenna pair comprising a second transmitting antenna element and a second receiving antenna element, the second transmitting antenna element being spaced from and connected to the second receiving antenna element by a second bridging segment,
    the first antenna pair and the second antenna pair being placed in spaced connection by a first spacing segment and a second spacing segment so that an open area is defined by the first antenna pair, the second antenna pair, the first spacing segment and the second spacing segment, wherein the first spacing segment connects a housing section of the first transmitting antenna element to a housing section of the second transmitting antenna element and the second spacing segment connects a housing section of the first receiving antenna element to a housing section of the second receiving antenna element, wherein the first spacing segment and the second spacing segment space the first antenna pair and the second antenna pair to create an area of reduced sensitivity between a first high sensitivity zone and a second high sensitivity zone, wherein the space between the first antenna pair and the second antenna pair is set so that the sensor is insensitive to fluid changes of a predetermined volume within the area of reduced sensitivity.

12. The sensor of claim 11 wherein each of the transmitting and receiving antenna elements is surrounded by the respective housing section, each of the transmitting and receiving antenna elements comprising a substrate mounted within the respective housing section and a generally planar antenna element mounted to the substrate.

13. The sensor device of claim 11 wherein a first area of higher sensitivity is defined by an area between the first transmitting antenna element and the first receiving antenna element and a second area of higher sensitivity is defined by an area between the second transmitting antenna element and the second receiving antenna element.

14. The sensor device of claim 11 further comprising an RF cable assembly for each of the antenna elements, each of the RF cable assemblies at one end thereof comprising a connector and at the other end thereof being electrically connected to the antenna element corresponding thereto.

15. The sensor device of claim 11 further comprising at least one flexible circuit board assembly for transmission of energy to and from the antenna elements.

16. The sensor device of claim 15 wherein the flexible circuit board comprises at least one splitter such that electromagnetic energy can be transmitted to the first transmitting antenna element and the second transmitting antenna element using a single transmission trace within the flexible circuit board.

17. The sensor device of claim 15 wherein the flexible circuit board comprises at least one combiner such that electromagnetic energy can be received from the first receiving antenna element and the second receiving antenna element and carried by a single transmission trace within the flexible circuit board.

18. The sensor of claim 11 further comprising an attachment mechanism to operably attach the sensor to the tissue of the body, the attachment mechanism comprising:

an adhesive portion defining a cutout region generally coextensive with the open area, the adhesive portion having one side thereof coated with a first adhesive adapted to removably attach to the tissue and an opposite side thereof coated with a second adhesive adapted to attach to the sensor.

19. The sensor of claim 18 wherein the attachment mechanism further comprises a release band affixed to a perimeter of the adhesive portion, the release band being generally free of adhesive.

* * * * *

UNITED STATES PATENT AND TRADEMARK OFFICE
CERTIFICATE OF CORRECTION

| | | |
|---|---|---|
| PATENT NO. | : 8,295,920 B2 | |
| APPLICATION NO. | : 10/576333 | |
| DATED | : October 23, 2012 | |
| INVENTOR(S) | : Bouton et al. | |

It is certified that error appears in the above-identified patent and that said Letters Patent is hereby corrected as shown below:

ON THE TITLE PAGE

On the Face Page, in Field (56), under "OTHER PUBLICATIONS", in Column 2, Line 1, delete "al.,"Extravasation" and insert -- al., "Extravasation --, therefor.

On the Face Page, in Field (74), under "Attorney, Agent, or Firm", in Column 2, Line 1, delete "Jim Denesvich" and insert -- Jill Denesvich --, therefor.

On Page 2, in Field (56), under "OTHER PUBLICATIONS", in Column 2, Line 2, delete "Fish"" and insert -- Fish," --, therefor.

IN THE SPECIFICATION

In Column 1, Line 18, delete "or," and insert -- or --, therefor.

In Column 1, Line 28, delete "invention" and insert -- invention. --, therefor.

In Column 1, Line 43, delete "example,)" and insert -- example, --, therefor.

In Column 3, Line 46, delete "is," and insert -- is --, therefor.

In Column 3, Line 56, delete "Determination"," and insert -- Determination," --, therefor.

In Column 6, Line 7, delete "antenna" and insert -- antenna. --, therefor. (second occurrence)

In Column 6, Line 17, delete "antenna" and insert -- antenna. --, therefor. (second occurrence)

In Column 6, Line 50, delete "antenna" and insert -- antenna. --, therefor. (first occurrence)

Signed and Sealed this
Nineteenth Day of February, 2013

Teresa Stanek Rea
*Acting Director of the United States Patent and Trademark Office*

CERTIFICATE OF CORRECTION (continued)
U.S. Pat. No. 8,295,920 B2

IN THE SPECIFICATION

In Column 7, Line 67, delete "extravasation;" and insert -- extravasation. --, therefor.

In Column 10, Line 19, delete "costs" and insert -- costs. --, therefor.

In Column 12, Line 51, delete "fall" and insert -- full --, therefor.

IN THE CLAIMS

In Claim 1, Column 15, Line 43, delete "the level" and insert -- a level --, therefor.

In Claim 1, Column 16, Line 2, delete "element" and insert -- element, --, therefor.

In Claim 11, Column 16, Line 53, delete "the level" and insert -- a level --, therefor.